United States Patent [19]

Negawa et al.

[11] Patent Number: 5,456,825
[45] Date of Patent: Oct. 10, 1995

[54] SIMULATED MOVING BED SEPARATION SYSTEM

[75] Inventors: Masakazu Negawa, Himeji; Fumihiko Shoji, Arai, both of Japan

[73] Assignee: Daicel Chemical Industries, Ltd., Japan

[21] Appl. No.: 85,444

[22] Filed: Jun. 30, 1993

[30] Foreign Application Priority Data

Jun. 30, 1992 [JP] Japan .................................. 4-172123
Jun. 30, 1992 [JP] Japan .................................. 4-172124

[51] Int. Cl.⁶ .............................. B01D 24/10; C07C 7/12
[52] U.S. Cl. ..................... 210/98; 210/136; 210/198.2; 210/253; 210/258; 210/287; 585/822
[58] Field of Search ........................... 210/97, 98, 117, 210/136, 198.2, 253, 258, 263, 264, 268, 287, 511; 585/820, 822, 825, 826

[56] References Cited

U.S. PATENT DOCUMENTS

| | | | |
|---|---|---|---|
| 2,985,589 | 5/1961 | Broughton et al. | |
| 5,122,275 | 6/1992 | Rasche | 210/198.2 |
| 5,126,055 | 6/1992 | Yamashita et al. | 210/198.2 |
| 5,200,075 | 4/1993 | Otani et al. | 210/283 |

FOREIGN PATENT DOCUMENTS

| | | |
|---|---|---|
| 0179970A1 | 5/1986 | European Pat. Off. |
| 0342629A1 | 11/1989 | European Pat. Off. |
| 0471082A1 | 2/1992 | European Pat. Off. |
| 92-16274 | 10/1992 | WIPO |

OTHER PUBLICATIONS

European Search Report for EP 93110371.7.

Primary Examiner—Robert A. Dawson
Assistant Examiner—W. L. Walker
Attorney, Agent, or Firm—Webb Ziesenheim Bruening Logsdon Orkin & Hanson

[57] ABSTRACT

An improved simulated moving bed separation system is disclosed. The improved novel system is characterized by being provided with rotary valves or check valves or both. The rotary valves are provided at the position where desorbing liquid is introduced, the position where the extract is taken out, the position where the feedstock is introduced and the position where the raffinate is taken out and the rotary valves are intermittently switched on and off, whereby the liquid take out of the unit packed bed preceding the position where the desorbing liquid is introduced is supplied to the circulation pump. The check valves are provided in the fluid flow passage between a unit packed bed and an extract draw-out port positioned in the next unit packed bed in the direction in the next unit packed bed in the direction of fluid flow. Thus liquid flow is smoothly controlled and the more effective separation is realized.

7 Claims, 2 Drawing Sheets

SIMULATED MOVING BED SEPARATION SYSTEM

FIELD OF THE INVENTION

The present invention relates to a simulated moving bed separation system having check valves, a simulated moving bed separation system having rotary valves, and simulated moving bed separation system having both check valves and rotary valve.

BACKGROUND OF THE INVENTION

Methods using a simulated moving bed separation system have been proposed for separating a desired component from a multicomponent mixture (see, for example, JP-B-42-15681).

In the simulated moving bed separation system proposed in the above-mentioned patent, there are provided four work zones packed with a solid adsorbent and connected to each other in a line, with the outlet of the fourth work zone being connected to the inlet of the first work zone so that a fluid can circulate through these four work zones. Also, a port for feeding a multi-component feedstock mixture to be treated into said work zones, a port for drawing out a weakly adsorbable component (raffinate) from said work zones, a port for supplying a desorbing liquid into the work zones and a port for drawing out the desorbing liquids and a strongly adsorbable component (extract from the work zones are provided so that the positions of the ports will advance simultaneously at given time intervals.)

The solid adsorbent packed in said work zones is a fine powder with a particle size of usually 15 mm or greater (see page 11, right column, lines 6–10 of JP-B-42-15681). Solid adsorbents with such a large particle size enable high-rate introduction of feedstock mixture and desorbing liquids. However, in order to accomplish separation at an even higher efficiency and higher rate by using the above simulated moving bed separation system, it is necessary to make smaller the particle size of the solid adsorbent. This, however, involves the difficult problems. When a solid adsorbent with a smaller particle size than those used hitherto is packed in the work zones and a feedstock mixture and a desorbing liquids are introduced into these work zones at high speed as in the prior art, there tends to occur a pressure loss in the work zones and back flow of the circulating fluid takes place in the work zones. Back flow of the circulating fluid causes a serious reduction of separating efficiency. Thus, when it is tried to improve the separating efficiency by reducing the particle size of the solid adsorbent, it is necessitated to drop the feed rate of the feedstock fluid into the work zones, and such drop of the feed rate decreases the separating efficiency to an intolerable level for industrial practice.

Also, in case the packing used in the simulated moving bed is already small in particle size, when the feedstock fluid charging rate is increased for further improving the separating efficiency, there takes place back flow of the circulating fluid as mentioned above to lower the separating efficiency.

Actually, many attempts have been made in recent years for separating optical isomers by using a simulated moving bed system of the described type. In these operations, and optical resolving agent with a very small particle size, which is in the order of one to several ten microns, is packed in the beds, and a feedstock mixture and a desorbing liquids are introduced at high rates in between the adjoining unit packed beds. In this case, the pressure loss by the packing is very great and the pressure at the outlet of a unit packed bed would become lower than the pressure of the desorbing liquid or feedstock fluid, causing such desorbing liquid or feedstock fluid to flow in the direction opposite to the flow of the circulating fluid.

The conventional simulated moving bed separation system, when described in other terms, comprises a plurality of unit packed beds connected in series to each other, in which a solution containing a feedstock mixture and a desorbing liquid are introduced into the packed bed containing an optical resolution packing therein and having front and rear ends thereof connected to each other endlessly via a fluid passage to circulate a fluid unidirectionally while at the same time drawing out a solution containing a separated component and a solution containing another component from the packed bed, wherein a port for introducing a desorbing liquids, a port for drawing out a solution containing a strongly adsorbable substance (extract), a port for introducing a solution containing a feedstock mixture, and a port for drawing out a solution containing a weakly adsorbable substance (raffinate) are arranged in the packed bed in this order along the direction of fluid flow and the positions of these ports are successively moved in the direction of fluid flow in the packed bed intermittently.

Also, in the conventional simulated moving bed separation system, in order to successively move said introducing a draw-out ports intermittently, there are provided four rotary valves, one for introducing a solution containing a feedstock mixture, on for introducing a desorbing liquids, one for drawing out an extract and one for drawing out a raffinate. Further, a circulation pump is disposed between a specific unit packed bed and another unit packed bed positioned downstream of said specific unit packed bed for circulating a fluid when moving said introducing and draw-out ports successively by switching said four rotary valves.

In operation of the simulated moving bed separation system, when the positions of said desorbing liquids introducing port, feedstock fluid introducing port, extract draw-out port and raffinate draw-out port are shifted by change-over operations of said rotary valves through a distance corresponding to one unit packed bed, the works to be performed in the respective unit packed beds, namely adsorption, concentration, desorbing and recovering of the desorbing liquids, are switched correspondingly. In each of said working steps, there is a setting flow rate which has been determined for accomplishing the desired separation.

Therefore, as the works to be performed in the respective unit packed beds are shifted by the rotary valve change-over operation, the flow rate of the circulation pump must be changed in accordance with the work to be performed.

It is essential that there is no difference between the circulation flow rate in the line preceding the circulation pump and the flow rate in the line succeeding said pump and between the feed rate into the circulation pump and the discharge rate from said pump. Therefore, the flow rate of the circulation pump must be adjusted stepwise synchronously with all of the other rotary valves upon every change-over operation of a rotary valve.

Thus, when the circulation pump was set between a specific unit packed bed and the adjoining unit packed bed on the downstream side, it was necessary to perform the troublesome operation of stepwise increasing or decreasing the fluid flow rate in the circulation pump upon every shifting of said introducing and draw-out ports in the direction of fluid flow.

The present invention has been made in view of the above circumstances.

Accordingly, the first object of the present invention is to provide a high-efficiency simulated moving bed separation system which is capable of separating a desired component from a feedstock mixture at high speed and high efficiency even when a feedstock fluid and a desorbing liquid are introduced at a high rate into an inlet port provided between a unit packed bed and the succeeding unit packed bed, each bed filed with a packing having a very small particle size.

The second object of the present invention is to provide a rotary valve-incorporated simulated moving bed separation system which has excellent operating performance and is suited for separating the individual components from a mixture of similar compounds and which can unnecessitate the conventional troublesome operation of stepwise adjusting the flow rate of the circulation pump upon every positional shifting of the introducing and draw-out ports.

SUMMARY OF THE INVENTION

The simulated moving bed separation system of this invention for attaining said first object comprises:

- a packed bed assembly, a first rotary valve, a second rotary valve, a third rotary valve, a fourth rotary valve, a circulation pump, and a fifth rotary valve;
- said packed bed assembly comprising a plurality of unit packed beds each containing a packing therein, said unit packed beds being connected in series to each other via a fluid passage and arranged to form a circulation passage for allowing unidirectional circulation of a fluid through the connected unit packed beds;
- said first rotary valve being designed to supply a feedstock fluid containing a weakly adsorbable substance and a strongly adsorbable substance to any selected one of the unit packed beds;
- said second rotary valve being designed to draw out a solution containing a weakly adsorbable substance, i.e. raffinate, from a unit packed bed positioned downstream of the unit packed bed to which the feedstock fluid has been supplied;
- said third rotary valve being designed to draw out a fluid from a unit packed bed positioned downstream of the unit packed bed from which the raffinate has been drawn out;
- said fourth rotary valve being designed to supply the fluid discharged out from said third rotary valve and a desorbing liquids into the unit packed bed adjoining to and downstream of the unit packed bed from which the fluid has been drawn out;
- said circulation pump being designed to transfer the fluid discharged out from said third rotary valve and a desorbing liquids to said fourth rotary valve;
- said fifth rotary value being designed to select a unit packed bed downstream of the unit packed bed to which the desorbing liquids has been supplied and draw out a solution containing a strongly absorbable substance, i.e. extract, from said selected unit packed bed;
- wherein the desorbing liquid supplying position, the extract draw-out position, the feedstock fluid feeding position and the raffinate draw-out position and shifted in succession intermittently without changing this order by the change-over operations of said first to fifth rotary valves.

The simulated moving bed separation system of this invention for attaining said second object comprises:

- a packed bed assembly comprising a plurality of unit packed beds connected in series to each other and each containing a packing therein, said unit packed beds having front and rear ends thereof connected to each other endlessly via a fluid passage to circulate a fluid unidirectionally;
- wherein a port for feeding a desorbing liquids, a port for drawing out solution containing a strongly absorbable substance (i.e. extract), a port for feeding a feedstock solution and a port for drawing out a solution containing a weakly absorbable substance (i.e. raffinate) are arranged in the packed bed in this order along the direction of fluid flow;
- a check valve is provided in the fluid passage between a unit packed bed and a desorbing liquids introducing port positioned preceding the next unit packed bed in the direction of fluid flow;
- a check valve is provided in the fluid passage between a unit packed bed and an extract draw-out port positioned preceding the next unit packed bed in the direction of fluid flow;
- a check valve is provided in the fluid passage between a unit packed bed and a feedstock solution introducing port positioned preceding the next unit packed bed in the direction of fluid flow;
- and a check valve is provided in the fluid passage between a unit packed bed and a raffinate draw-out port positioned preceding the next unit packed bed in the direction of fluid flow.

DESCRIPTION OF THE PREFERRED EMBODIMENTS

The present invention is described more particularly below.

A. Simulated moving bed

Figure 1:
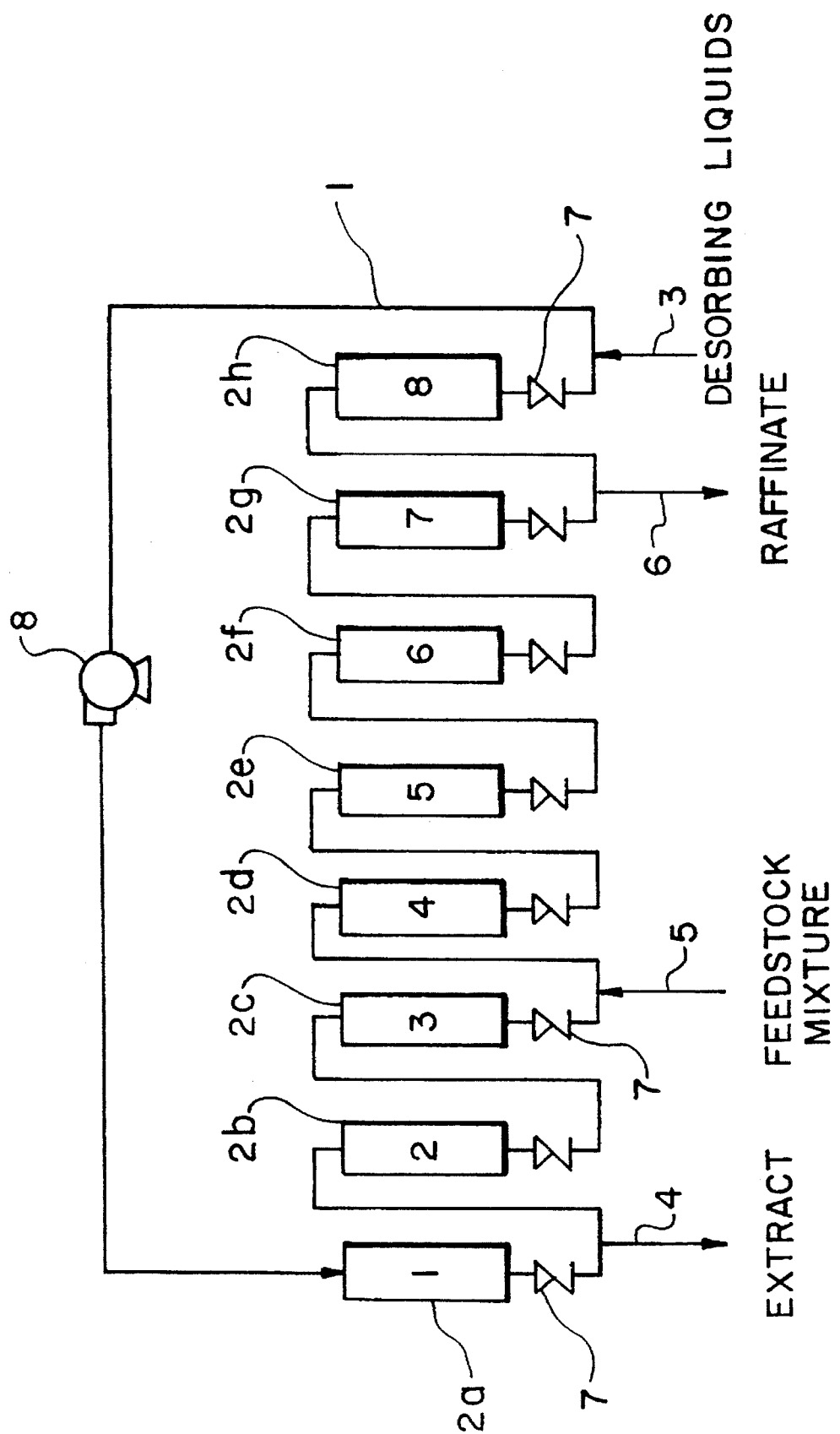
FIG. 1 is a schematic diagram showing the concept of the simulated moving bed separation system according to the present invention.

The simulated moving bed according to the present invention, as illustrated in FIG. 1, comprises a packed bed assembly consisting of a plural number (for example, 12 or 8) of unit packed beds $2a$–$2h$ arranged in series to each other in a fluid passage 1 through which a fluid is circulated. In the fluid passage, a fluid is circulated in one direction. The number of the unit packed beds used in the system is not defined; it may be properly selected in consideration of the scale of practice, adsorption technique and other matters.

In this packed bed system, as shown in FIG. 1, a port 3 for introducing a desorbing liquids, a port 4 for drawing out a solution containing a substance strongly adsorbable on the packing, i.e. an extract, a port 5 for introducing a feedstock fluid and a port 6 for drawing out a solution containing a substance weakly adsorbable on the packing, i.e. a raffinate, are arranged in this order and designed so that the positions of these ports can be successively changed in the direction of fluid flow in the packed bed intermittently.

Also, in the present invention, in the fluid passage 1 connecting the respective unit packed beds $2a$–$2h$ with the adjoining ones, a check valve 7 is provided between each of the desorbing liquids introducing port 3 and feedstock fluid introducing port 5 and the unit packed bed positioned upstream thereof.

In the simulated moving bed separation system shown in FIG. 1, the desorbing liquid introducing port 3 is connected to a section of the fluid passage 1 communicating the 8th unit packed bed 2h and the first unit packed bed 2a, the extract draw-out port 4 is connected to a section of the fluid passage 1 communicating the first unit packed bed 2a and the second unit packed bed 2b, the feedstock fluid introducing port 5 is connected to a section of the fluid passage 1 communicating the third unit packed bed 2c and the fourth unit packed bed 2d, and the raffinate draw-out port 6 is connected to a section of the fluid passage 1 communicating the seventh unit packed bed 2g and the eighth unit packed bed 2h. For successively moving these introducing and draw-out ports along the direction of fluid flow intermittently, there are used, for example, rotary valves. Also, a recycle pump 8 or like means is employed for circulating a fluid through the fluid passage 1 in this simulated moving bed separation system.

Type, etc., of the packing

In each of the unit packed beds is contained a packing which is capable of adsorbing a substance to be separated.

For instance, in case of separating an optical isomer mixture, there can be employed the optical resolution packings using the optically active high-molecular weight compounds or low-molecular weight compounds having optical resolving power. Said optically active high-molecular weight compounds include esters and carbamates of cellulose or amylose, polysaccharide derivatives such as carbamates and esters, polyacrylate derivatives and polyamide derivatives. For use as packing, these compounds are carried on silica gel or powdered and otherwise worked into a particulate preparation without using silica gel. The low-molecular weight compounds having optical resolving power include crown ethers and their derivatives, cyclodextrin and its derivatives, and the like. These low-molecular weight compounds are usually supported on a carrier such as silica gel for use as packing.

The following are the preferred examples of the commercially available optical resolution packings: CHIRALCEL OB (trade name), CHIRALCEL OD (trade name), CROWNPAK CR (+) (trade name), CHIRALCEL CA-1 (trade name), CHIRALCEL OA (trade name), CHIRALCEL OK (trade name), CHIRALCEL OJ (trade name), CHIRALCEL OC (trade name), CHIRALCEL OF (trade name), CHIRALCEL OG (trade name), CHIRALPAK WH (trade name), CHIRALPAK WM (TRADE NAME), CHIRALPAK WE (trade name), CHIRALPAK OT (+) (trade name), CHIRALPAK OP (+) (trade name), CHIRALPAK AS (trade name) and CHIRALPAK AD (trade name), all produced by Daicel Chemical Industries, Ltd.

As examples of the packings suited for resolving an isomerized saccharide solution containing oligosaccharide, there can be cation exchange resins for alkaline earth metal (calcium, barium, strontium, etc.) salt type strong acids and crystalline aluminosilicates such as zeolite Y in which exchangeable cations are substituted with ammonium, sodium, potassium, calcium, strontium, barium saccharide or the like.

As examples of the packings suited for separating fatty acids and triglycerides, there can be mentioned anion exchange resins having a styrene-divinylbenzene copolymer as skeleton. Examples of the commercially available packing of this type include Amberlite IRA 93 produced by Rohm & Haas, Ltd., and Duolite A377 produced by Sumitomo Chemical Industries, Ltd., which are weakly anion exchange resins, and Amberlite IRA 400 (Rohm & Haas) and Duolite A161 (Sumitomo Chem. Ind.) which are strongly anion exchange resins.

It is possible to use various other known types of packings which are considered useful for separating various types of material.

Particles size of the packing

The average particle size of the packing is variable depending on the type of the component to be separated, volumetric flow rate of the solvent supplied into the simulated moving bed and other matters, but usually it is in the range of 1 to 100 µm, preferably 5 to 75 µm. For confining pressure loss in a restricted range in the simulated moving bed, it is desirable to adjust the average particle size of the packing to be 15 to 75 µm. when the average particle size of the packing is within the above range, pressure loss in the simulated moving bed can be reduced, for example, to the order of 10 kgf/cm$^2$ or less. On the other hand, the greater the average particle size of the packing, the less becomes the absorption theoretical plate number. When the practical attainment of the absorption theoretical plate number alone is considered, the average particle size of the packing is usually in the range of 1 to 50 µm.

Desorbing liquid

The desorbing liquids usable in the system of the present invention include organic solvents, for example, alcohols such as methanol, ethanol and isopropanol hydrocarbons such as hexane, etc., mixed organic solvents consisting of hydrocarbons and alcohols, halides, ethers or esters, and aqueous solutions containing a salt such as copper sulfate solution, perchlorate solution, phosphoric acid solution, etc. The desorbing liquid actually used is decided according to the type of the component or compound to be separated.

Component or substance to be separated

The feedstock fluids that can be treated in the separation system of the present invention are not subject to any specific restrictions. They include various kinds of compounds used in the fields of medicine, agricultural chemicals, food, feed, perfume and the like. To cite some typical examples, they include thalidomide which is a medicinal preparation, EPN which is an organophosphorus agricultural chemical, monosodium salt of glutamic acid which is a chemical seasoning, and menthol which is a perfume. They also include optically active alcohols and esters.

Among other feedstock fluids that can be separated by the simulated moving bed separation system of this invention are a mixture of normal hexane and cyclohexane, mixtures of the compounds which are close to each other in boiling points, for example, a normal compound and its isomers, as in the case of hydrocarbons, alcohols, aldehydes and ketones, aqueous solutions containing dextrose or the like and fructose, and mixtures of maltose and polysaccharides such as maltotriose or saccharides with higher molecular weight.

Process in simulated moving bed separation system

Absorption and desorption of a substance in a feedstock mixture by the simulated moving bed separation system according to the present invention are accomplished by cyclic operations of the following basic steps: absorption, concentration, desorption and recovery of desorbing liquid, which are described below.

(1) Absorption

The feedstock fluid is contacted with the packing so that a strongly absorbable component is adsorbed on the packing while another weakly absorbable component is recovered as a raffinate together with the desorbing liquids.

(2) Concentration

The packing having the strongly adsorbable component adsorbed thereon is contacted with part of the extract described below so that the weakly adsorbable component remaining on the packing is expelled and the strongly adsorbable component is concentrated.

(3) Desorption

The packing containing the concentrated strongly adsorbable component is contacted with the desorbing liquids so that the strongly adsorbable component is expelled from the packing and discharged out from the simulated moving bed as an extract together with the desorbing liquids.

(4) Desorbing liquids recovery

The packing having substantially only the desorbing liquids adsorbed thereon is contacted with part of the raffinate so that part of the desorbing liquids contained in the packing is recovered as a desorbing liquids recovery flow.

The present invention is further described below with reference to the drawings.

Figure 2:
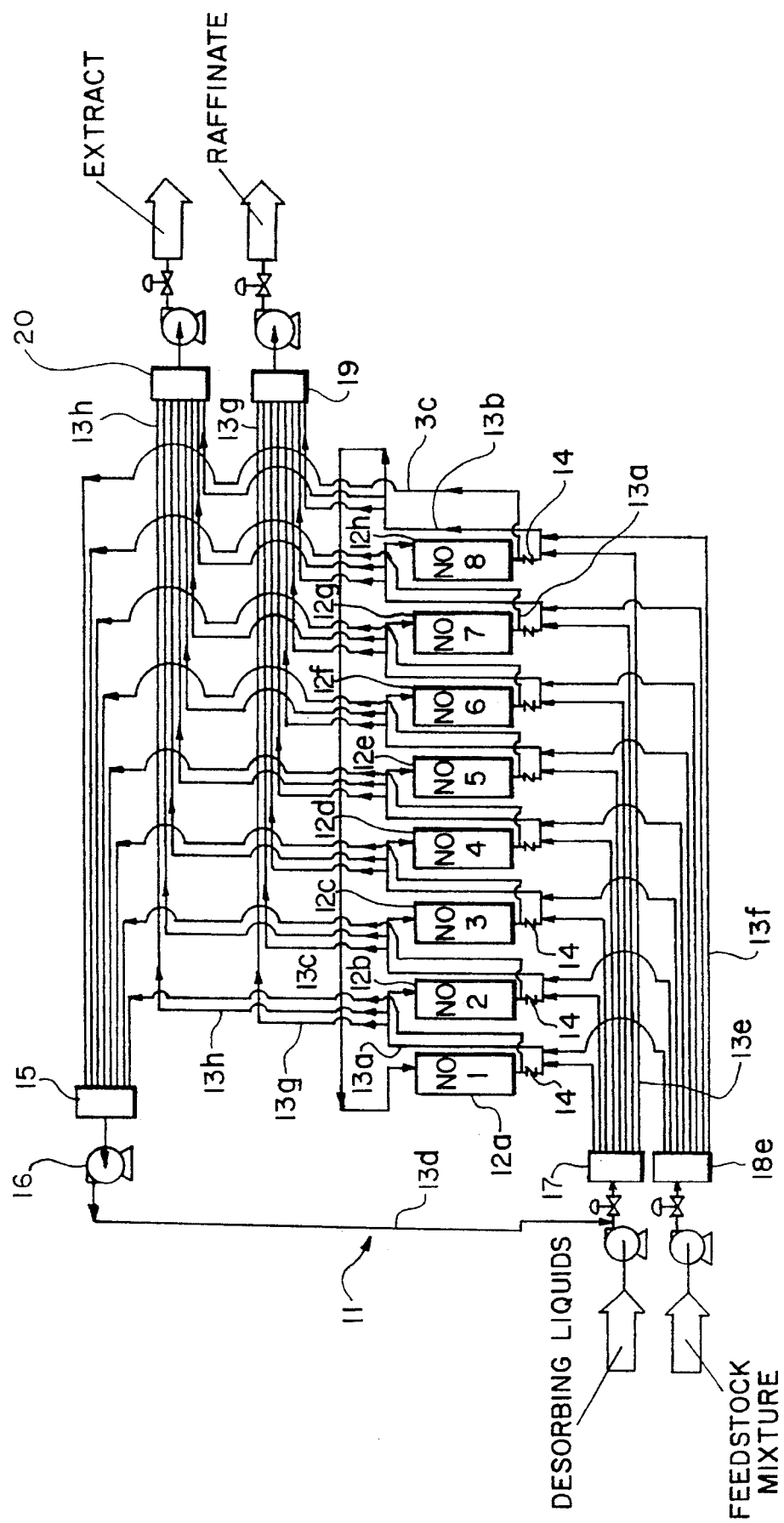
FIG. 2 is a schematic diagram showing an embodiment of the simulated moving bed separation system of this invention provided with check valves and rotary valves.

As shown in FIG. 2, the simulated moving bed separation system 11 according to an embodiment of this invention comprises the first to eighth unit packed beds 12a–12h. These unit packed beds are connected to each other by a fluid passage 13a. The eighth unit packed bed 12h and the first unit packed bed 12a are connected by a fluid passage 13a. A check valve 14 is provided in the fluid passage 13a connecting one unit packed bed to the next unit packed bed. This check valve 14 allows passage of a fluid from one unit packed bed to the next but checks its backward flow.

A fluid passage 13c connected to a third rotary valve 15 branches from a section of the fluid passage 13a between a unit packed bed and the associated check valve 14. In other words, a fluid passage 13c branching from the fluid passage 13a communicating the first and second unit packed beds 12a and 12b, a fluid passage 13c branching from the respective fluid passages 13a communicating the corresponding unit packed beds are connected to the third rotary valve 15. This third rotary valve 15 functions to select one fluid passage from the total 8 branching fluid passages 13c and draw out the fluid from the selected fluid passage 13c while leaving the other fluid passages 13c closed.

A circulation pump 16 is connected to the discharge side of said their rotary valve 15. The discharge side of said circulation pump 16 is connected to a fourth rotary valve 17 via a fluid passage 13d.

A desorbing liquids is supplied along with the fluid from said circulation pump 16 to the fourth rotary valve 17. Eight fluid passages 13e extend from the discharge side of said fourth rotary valve 17, each of said fluid passages 13e being connected to a section of the fluid passage 13e between the associated check valve 14 and the next unit packed bed.

A feedstock solution is supplied to a first rotary valve 18 via a pump. Eight fluid passages 13f connect to the discharge side of said first rotary valve 18, each of said fluid passages 13f being connected to a section of the corresponding fluid passage 13a between the associated check valve 14 and the next unit packed bed.

Also, a fluid passage 13g connected to a second rotary valve 19 branches from a section of the corresponding fluid passage 13a between the associated check valve 14 and the next unit packed bed. Total 8 fluid passages 13g branching from the respective fluid passages 13a connect to said second rotary valve 19 which functions to open one of said branched fluid passages 13g while keeping the reset of them closed. A fluid is discharged out from this second rotary valve 19 by a pump.

Further, a fluid passage 13h connecting to a fifth rotary valve 20 branches from a section of the corresponding fluid passage 13a between the associated check valve 14 and the next unit packed bed. Total 8 fluid passages 13h branching from the respective fluid passages 13a are connected to said fifth rotary valve 20 which functions to open one of said fluid passages 13h while keeping the rest of the closed.

In the simulated moving bed separation system 11 shown in FIG. 2, the first to fifth rotary valves 15–20 are set to function as described below.

The fourth rotary valve 17 functions to select one fluid passage 13e so that the corresponding fluid passage 13b communicating the eight unit packed bed 12h with the first unit packed bed 12a while the other fluid passages 13a are left closed. The fifth rotary valve 20 operates to select a fluid passage 13h so that only the fluid passage 13h branching from the fluid passage 13a communicating the first and second unit packed beds is brought into an open state while leaving the other fluid passages 13h in a closed state. In the case of the first rotary valve 18, one fluid passage 13f is selected so that only the fluid passage 13f connected to the fluid passage 13a communicating the third and fourth unit packed beds 12c and 12d is opened while the other fluid passages 13f are left closed. The second rotary value 19 functions to select one fluid passage 13g so that only the fluid passage 13g branching from the fluid passage 13a communicating the seventh and eight unit packed beds 12g and 12h is opened while the other fluid passages 13g are kept closed, and the third rotary valve 15 functions to select one fluid passage 13c so that only the fluid passage 13c between the eight unit packed bed 12h and the associated check valve 14 is opened while the other fluid passages 13c are left closed.

Said first to fifth rotary valves 15, 17–20 are synchronized in operation by a control device not shown in the drawing. A computer programmed to effect synchronous operation of the first to fifth rotary valves or a similarly programmed relay system sequencer may be used as the control device.

Each of said unit packed beds contain a packing which is capable of adsorbing the component to be separated.

In the simulated moving bed system shown in FIG. 2, with the first to fifth rotary valves 15, 17–20 being operated to produce the above-described open and closed states, when a desorbing liquid is supplied through the fourth rotary valve 17 into the fluid passage 13b communicating the eighth and first unit packed beds 12h and 12a, the associated check valve 14 performs its back flow checking function and the fluid discharged from the eighth unit packed bed 12h is led through the fluid passage 13c to the third rotary valve 15 and thence said fluid is passed through the circulation pump 16, fourth rotary valve 17, fluid passage 13e and fluid passage 13b and introduced into the first unit packed bed 12a.

In operation of the simulated moving bed separation system illustrated in FIG. 2, in the initial adsorption step, a feedstock mixture is contacted with the packing by the fourth to seventh unit packed beds 12d–12g and a strongly adsorbable component is adsorbed on the packing while other weakly adsorbable component is recovered as a raffinate together with the desorbing liquids. Then, in the concentration step, the packing having the strongly adsorbable component adsorbed thereon by the second and third unit packed beds 12b and 12c is contacted with part of the extract so that the weakly adsorbable component remaining on the packing is expelled and the strongly adsorbable component is concentrated. In the next desorption step, the packing containing unit packed bed 12a so that the strongly adsorbable unit packed bed 12a so that the strongly adsorbable component is expelled from the packing and discharged out from the simulated moving bed as an extract together with the desorbing liquids. In the final desorbing liquids recovery step, the packing having substantially only the desorbing liquids adsorbed thereon is contacted with part of the raffinate by the eighth unit packed bed 12h so that part of the desorbing liquids contained in the packing is recovered as a recovery product.

In this simulated moving bed separation system 11, the desorbing liquids supplying position, the feedstock fluid supplying position and the respective draw-out positions are shifted through a distance corresponding to one unit packed bed in the direction of solvent flow by manipulating the first to fifth rotary valves 15–20 at given time intervals.

Thus, in the second stage, desorption is performed by the second unit packed bed 12b, concentration by the third and fourth unit packed beds 12c and 12d, adsorption by the fifth to eight unit packed beds 12e–12h, and desorbing liquids recovery by the first unit packed bed 12a. As these operations are performed successively, the positions of said works are shifted through a distance corresponding one unit packed bed and the separation of a mixture of the similar compounds is accomplished continuously and efficiently.

Also, in the present simulated moving bed separation system 11, the amount of the fluid drawn out from each unit packed bed through the fluid passage 13b is fixed, so that there is no need of adjusting the discharge rate of the circulation pump 16 connected to the third rotary valve 15 upon every changeover of said third rotary valve 15.

Further, in this simulated moving bed separation system 11, a check valve is provided between each feed stock fluid or desorbing liquids feed line and the fluid outlet of each unit packed bed, so that even if a pressure loss is caused for the fluid by the packing contained in each unit packed bed, there is no possibility that the fluid supplied from each feed line to a fluid passage should flow backwardly to the upstream unit packed bed.

Thus, when using the simulated moving bed separation system of this invention, even if a packing with fairly small particle size is contained in each unit packed bed, there occurs no back flow of the fluid and smooth operation of the system is accomplished, so that improvement of separating efficiency due to use of a fine packing and long-time continuous operation due to no occurrence of back flow of the circulating fluid are realized.

EXAMPLE 1

1-Phenylethyl alcohol was fed as a solution containing an optical isomer mixture at a rate of 1 ml/min (total concentration of isomer: 21 mg/ml) into a simulated moving bed apparatus such as shown in FIG. 2 which was comprised of 8 connected columns, as unit packed beds, each having an inner diameter of 2 cm and a length of 25 cm and containing a packing for separation of an optical isomer (CHIRALCEL OD) having a particle diameter of 20 μm, manufactured by Diacel Chemical Industries, Ltd.). As a desorbing liquids, a hexane/isopropanol (90/10 v/v %) mixture was fed at a rate of 32.1 ml/min. The solvent circulated in the solvent circulation line was the same as the desorbing liquids.

As a result, an extract containing a strongly adsorbable optical isomer in a concentration of 0.36 mg/ml at an optical purity of 94% e.e. was obtained at a rate of 28.2 ml/min from the extract draw-out port in the above simulated moving bed apparatus.

Also, a raffinate containing a weakly adsorbable optical isomer in a concentration of 2.2 mg/ml at an optical purity of 99.9% e.e. was obtained at a rate of 4.9 ml/min from the raffinate draw-out port in the above apparatus.

COMPARATIVE EXAMPLE 1

The procedure of Example 1 was followed using the same simulated moving bed apparatus as shown in FIG. 2 except that no check valve was provided.

As a result, an extract containing a strongly adsorbable optical isomer in a concentration of 0.395 mg/ml at an optical purity of 46% e.e. was obtained at a rate of 28.2 ml min from the extract draw-out port in this simulated moving bed apparatus.

Also, a raffinate containing a weakly adsorbable optical isomer in a concentration of 2.014 mg/ml at an optical purity of 52% e.e. was obtained at a rate of 4.9 ml/min from the raffinate draw-out port.

INDUSTRIAL APPLICABILITY

In the simulated moving bed separation system according to the present invention, as it is provided with check valves, there takes place no back flow of the circulating fluid toward the upstream unit packed beds when a desorbing liquids and a feedstock fluid are supplied to the circulation lines from the respective feed lines, so that a smooth separating operation free of trouble due to occurrence of back flow is realized. Also, since back flow of the circulating fluid is prevented, it becomes possible to use a packing with a small particle diameter which will not induce a large pressure drop in the unit packed beds, and by filling the unit beds with such a fine packing, it is possible to attain a phenomenal improvement of separating efficiency.

Further, according to the present invention, there is provided a rotary valve-incorporated simulated moving bed separation system in which the fluid left after draw-out of a raffinate by a second rotary valve is circulated in a packed bed assembly consisting of a plurality of unit packed beds by a third rotary valve and a circulation pump, so that when the desorbing liquids feed position, the feedstock fluid feed position, the extract draw-out position and the raffinate draw-out position are changed for each of the unit packed beds, there is no need of adjusting the flow rate of the fluid circulated by the circulation pump, and further since the first to fifth rotary valves are changed over synchronously with each other, the operation of this simulated moving bed system is very simplified and it is also possible to efficiently separate a desired component in a mixture.

What is claimed is:

1. A simulated moving bed separation system comprising:

a packed bed assembly, a first rotary valve, a second rotary valve, a third rotary valve, a fourth rotary valve, a circulation pump, and a fifth rotary valve, said packed bed assembly comprising a plurality of unit packed beds each containing a packing therein, said unit packed beds being connected in series to each other via a fluid passage and arranged to form a circulation passage for allowing unidirectional circulation of a fluid through the connected unit packed beds;

said first rotary valve having an inlet and a plurality of outlets, with each of said outlets being connected to a separate unit packed bed, whereby said first rotary valve is coupled to each of said unit packed beds, said first rotary valve being designed to supply a feedstock fluid containing a weakly adsorbable substance and a strongly adsorbable substance to any selected one of the unit packed beds in said packed bed assembly;

said second rotary valve having an outlet and a plurality of inlets, with each of said inlets being connected to a separate unit packed bed, whereby said second rotary valve is coupled to each of said unit packed beds, said second rotary valve being designed to draw out a solution containing a raffinate, which is a weakly adsorbable substance, from the unit packed bed positioned downstream of the unit packed bed to which the feedstock fluid has been supplied;

said third rotary valve having an outlet and a plurality of inlets, with each of said inlets being connected to a separate unit packed bed, whereby said third rotary valve is coupled to each of said unit packed beds, said third rotary valve being designed to draw out a fluid from the unit packed bed positioned downstream of the unit packed bed from which a raffinate has been drawn out;

said fourth rotary valve having an inlet and a plurality of outlets, with each of said outlets being connected to a separate unit packed bed, whereby said fourth rotary valve is coupled to each of said unit packed beds, said fourth rotary valve being designed to supply the fluid discharged out from said outlet of said third rotary valve and desorbing liquids to the unit packed bed positioned downstream of the unit packed bed from which a fluid has been drawn out;

said circulation pump disposed between said outlet of said third rotary valve and said inlet of said fourth rotary valve, said circulation pump being designed to transfer the fluid discharged out from said outlet of said third rotary valve to said inlet of said fourth rotary valve;

said fifth rotary valve having an outlet and a plurality of inlets, with each of said inlets being connected to a separate unit packed bed, whereby said fifth rotary valve is coupled to each of said unit packed beds, said fifth rotary valve being designed to select a unit packed bed downstream of the unit packed bed to which a desorbing liquid has been supplied and draw out a solution containing an extract, which is a strongly adsorbable substance, from said selected unit packed bed;

wherein the desorbing liquids supplying position, the extract draw-out position, the feedstock fluid supplying position and the raffinate draw-out position are shifted in succession intermittently without changing this order by the change-over operations of said first to fifth rotary valves, and the discharge rate of said circulation pump is constant during change-over of said third rotary valve.

2. A simulated moving bed separation system as set forth in claim 1, wherein said packing includes a plurality of particles having an average particle size within the range of about 1 to 100 μm.

3. A simulated moving bed separation system according to claim 2, wherein said particle size is between 1 to 50 μm.

4. A simulated moving bed separation system comprising:
a packed bed assembly, a first rotary valve, a second rotary valve, a third rotary valve, a fourth rotary valve, a circulation pump, a fifth rotary valve and a control means, said packed bed assembly comprising a plurality of unit packed beds, wherein the fluid outlets of said unit packed beds and the fluid inlets of the adjoining unit packed beds are connected by piping to form an endless circulation passage;

said first rotary valve coupled to each said unit packed bed, wherein said first rotary valve is provided with a same number of discharge ports as the unit packed beds and one suction port, each of said discharge ports being connected to a feed line connected to a pipe connecting the fluid outlet of a unit packed bed and the fluid inlet of the adjoining unit packed bed, said rotary valve being designed so that a feedstock fluid containing a weakly adsorbable substance and a strongly adsorbable substance may be supplied to any selected one of said unit packed beds by switching the discharge ports of said valve;

said second rotary valve coupled to each said unit packed bed, wherein said second rotary valve is provided with a same number of suction ports as the unit packed beds and one discharge port, each of said suction ports being connected to a pipe connecting the fluid outlet of a unit packed bed and the fluid inlet of the adjoining unit packed bed to a discharge line connected to a pipe extending from the joint with the feed line connected to the discharge ports of said first rotary valve to the fluid inlet of the adjoining unit packed bed, said secondary rotary valve being designed so that by switching the suction ports thereof, a solution containing a raffinate, which is a weakly adsorbable substance, is drawn out from a discharge line connected to the fluid outlet of a unit packed bed positioned downstream of the unit packed bed to which the feedstock fluid has been supplied from the pipe connected to a discharge port of said first rotary valve;

said third rotary valve coupled to each said unit packed bed, wherein said third rotary valve is provided with a same number of suction ports as the unit packed beds and one discharge port, each of said suction ports being connected to a discharge line branching from a pipe connecting the fluid outlet of a unit packed bed and the fluid inlet of the adjoining unit packed bed, at a point of said pipe joined to the feed line connected to the discharge ports of said first rotary valve, so that a fluid can be drawn out from the unit packed bed positioned downstream of the unit packed bed from which the raffinate has been drawn out;

said fourth rotary valve coupled to each said unit packed bed, wherein said fourth rotary valve is provided with a same number of discharge ports as the unit packed beds and one suction port, each of said discharge ports being connected to a feed line connected to a point between the position where the pipe connecting the fluid outlet of a unit packed bed and the fluid outlet of the adjoining unit packed bed is joined to the feed line connected to the discharge ports of said first rotary valve and the position where the discharge line of the third rotary valve branches, whereby the fluid discharged out from said third rotary valve and a separately supplied desorbing liquid are sucked in from said suction port and discharged from the discharge ports so as to be supplied through said feed line to the unit packed bed positioned downstream of the unit packed bed from which the fluid has been drawn out;

said circulation pump disposed between said outlet of said third rotary valve and said inlet of said fourth rotary valve, said circulation pump being designed to transfer the fluid discharged out from said outlet of said third rotary valve to said inlet of said fourth rotary valve;

said fifth rotary valve coupled to each said unit packed bed, wherein said fifth rotary valve is provided with a same number of suction ports as the unit packed beds and one discharge port, each of said suction ports being connected to a discharge line connected to a pipe connecting the fluid outlet of unit packed bed and the fluid inlet of the adjoining unit packed bed, at a point of said pipe between the position where said pipe is joined to the discharge line of the second rotary valve and the fluid inlet of the adjoining unit packed bed, whereby a unit packed bed positioned downstream of the unit packed bed to which the desorbing liquid has been supplied is selected and a solution containing an extract, which is a strongly adsorbable substance, is drawn-out from the selected unit packed bed;

said control means being adapted to control the change-over operations of said first to fifth rotary valves so that the desorbing liquid supply position, the extract draw-out position, the feedstock fluid supply position and the raffinate draw-out position will be successively shifted in this order intermittently; and the discharge rate of said circulation pump is maintained constant during change-over of said third rotary valve.

5. A simulated moving bed separation system as set forth in claim 4, wherein each said unit packed bed includes a packing including a plurality of particles having an average particle size within the range of about 1 to 100 μm.

6. A simulated moving bed separation system as set forth in claim 5, wherein said average particle size is within the range of 1 to 50 μm.

7. A simulated moving bed separation system set forth in claim 4, wherein a check valve is provided in a pipe connecting the fluid outlet of a unit packed bed and the fluid inlet of the adjoining unit packed bed, at a point of said pipe between the position where said pipe is joined to the discharge line connected to the suction ports of the third rotary valve and the position where said pipe is joined to the feed line connected to the discharge ports of the first rotary valve, whereby said check valves prevent fluid passage in the direction opposite the direction of fluid flow.

* * * * *